US012728233B2

(12) United States Patent
Van Damme et al.

(10) Patent No.: US 12,728,233 B2
(45) Date of Patent: Sep. 8, 2026

(54) CATHETER RETAINING DEVICE

(71) Applicant: Bedal NV, Diepenbeek (BE)

(72) Inventors: Alexander Van Damme, Zoersel (BE); Simon Callaerts, Leuven (BE)

(73) Assignee: BEDAL NV, Diepenbeek (BE)

( * ) Notice: Subject to any disclaimer, the term of this patent is extended or adjusted under 35 U.S.C. 154(b) by 1058 days.

(21) Appl. No.: 17/779,815

(22) PCT Filed: Nov. 27, 2020

(86) PCT No.: PCT/EP2020/083714

§ 371 (c)(1),
(2) Date: May 25, 2022

(87) PCT Pub. No.: WO2021/105415

PCT Pub. Date: Jun. 3, 2021

(65) Prior Publication Data

US 2023/0001153 A1 Jan. 5, 2023

(30) Foreign Application Priority Data

Nov. 29, 2019 (EP) .................................... 19212594

(51) Int. Cl.
*A61M 25/02* (2006.01)

(52) U.S. Cl.
CPC ..... *A61M 25/02* (2013.01); *A61M 2025/0206* (2013.01); *A61M 2025/024* (2013.01); *A61M 2025/0246* (2013.01); *A61M 2025/0266* (2013.01); *A61M 2025/028* (2013.01)

(58) Field of Classification Search
CPC ............ A61M 25/02; A61M 2025/024; A61M 2025/0246; A61M 2025/0253; A61M 2025/0266; A61M 2025/0273; A61M 2025/0206; A61M 2025/028
See application file for complete search history.

(56) References Cited

U.S. PATENT DOCUMENTS 3,696,920 A * 10/1972 Lahay .................... A61B 50/30 206/370
5,643,217 A * 7/1997 Dobkin .................. A61B 17/00 604/174
6,213,979 B1 * 4/2001 Bierman ............... A61M 25/02 604/177
6,458,104 B2 * 10/2002 Gautsche ............... A61B 46/23 604/179

(Continued)

FOREIGN PATENT DOCUMENTS

JP 2009078166 A 8/2012
KR 20180052327 A * 5/2018 ............ A61M 1/008
KR 201800582327 A 5/2018

OTHER PUBLICATIONS

KR20180052327A—Machine Translation of the Specification (Year: 2018).*

(Continued)

*Primary Examiner* — William R Carpenter
*Assistant Examiner* — Robert F Allen
(74) *Attorney, Agent, or Firm* — DINSMORE & SHOHL LLP

(57) ABSTRACT

The present invention relates to means for fixating catheters, which are used in healthcare and in particular to means (1,5) for fixating such catheters to a living creature.

15 Claims, 4 Drawing Sheets

(56) References Cited

U.S. PATENT DOCUMENTS 7,232,427 B2 * 6/2007 Propp .................. A61M 25/02 128/849
7,320,681 B2 * 1/2008 Gillis .................. A61M 25/02 604/174
7,879,013 B2 * 2/2011 Smith .................. A61M 25/02 604/174
8,052,648 B2 * 11/2011 Dikeman .............. A61M 25/02 604/174
8,211,064 B2 * 7/2012 Sloan .................. A61M 25/02 604/179
8,556,859 B2 * 10/2013 Nilson .................. A61M 25/02 604/174
9,463,303 B2 * 10/2016 Nilson .................. A61M 25/02
10,799,679 B2 * 10/2020 Roberts ................ A61M 25/02
11,331,453 B1 * 5/2022 Drake .................. A61M 25/02
2001/0049504 A1 * 12/2001 Gautsche .............. A61B 46/23 604/179
2005/0182368 A1 * 8/2005 Gillis .................. A61M 25/02 128/DIG. 26
2005/0277888 A1 * 12/2005 Propp .................. A61M 25/02 604/174
2007/0142784 A1 * 6/2007 Dikeman .............. A61M 25/02 604/174
2007/0265572 A1 * 11/2007 Smith .................. A61M 25/02 604/174
2009/0024090 A2 * 1/2009 Wright .................. A61M 25/02 604/174
2009/0182283 A1 * 7/2009 Sloan .................. A61M 25/02 604/180
2013/0165863 A1 * 6/2013 Nilson .................. A61M 25/02 604/174
2018/0154117 A1 * 6/2018 Roberts ................ A61M 25/02
2023/0310808 A1 * 10/2023 Jansson ................ A61M 25/02 604/179
2023/0310809 A1 * 10/2023 Van Damme ......... A61M 25/02 604/179

OTHER PUBLICATIONS

International Search Report mailed Feb. 8, 2021 in reference to co-pending European Application No. PCT/EP2020/083714 filed Nov. 27, 2020.
European Search Report in reference to European Application No. 19212594, filed Nov. 27, 2020.

* cited by examiner

CATHETER RETAINING DEVICE

CROSS REFERENCES TO RELATED APPLICATIONS

This application is a national-stage application under 35 U.S.C. § 371 of International Application No. PCT/EP2020/083714, filed Nov. 27, 2020, which International Application claims benefit of priority to European Patent Application No. 19212594.6, filed Nov. 29, 2019.

FIELD OF THE INVENTION

The present invention relates to means for fixating different types of catheters, which are used in healthcare and in particular to means for fixating such catheters to a living creature.

BACKGROUND TO THE INVENTION

In healthcare, a catheter is used to provide an access to the human body for drainage of a bodily fluid or for delivery of medicinal drugs, parenteral nutrition, blood or blood components or other liquids. A catheter is typically used for patients that are ill or during the performance of surgical procedures. Depending on the goal which is desired to be achieved and sometimes also depending on the patient or his/her medical condition, different catheters and different application methods can be selected.

KR20180052327 discloses a medical tube securing clip for securing a drain tube inserted from a drain tube of a medical low-pressure continuous aspirator and inserted into a lesion portion. Another specific type of catheter is the epidural catheter, which is mainly used for drug administration such as epidural anesthesia or contrast agents. Epidural anesthesia can be injected into the epidural space around the spinal cord. These epidural catheters are than placed into the epidural space, and sometimes have to stay in place for several days. Both a correct introduction of the catheter and a correct fixation of the catheter are matters of utmost importance.

A second type of catheter is the peripheral nerve block catheter, which is a catheter which closely resembles the epidural catheter and being mainly used for local anesthesia.

Another type of catheter is the peripherally inserted central venous catheter for premature babies and neonates being mainly suitable for the delivery of medication and/or parenteral nutrition. These types of catheters generally have a French size (Fr) or gauge value with a maximum residing around 5 Fr and 16 (G) respectively, which corresponds to an external diameter of about 1.67 millimeters.

A disadvantage of the securement of catheters to a patient is that it often is a burden for patients in terms of wearing comfort. For example, excessive movement whilst a catheter or part thereof is applied to the human body may be difficult to nearly impossible as the position of the catheter within the body should under all circumstances remain fixed. Accidental catheter removal, upon the exertion of a pulling force should be avoided. Also, a change in position of the catheter (e.g. catheter dislocation or migration) may prevent proper operation and in some circumstances could even lead to dangerous or life-threatening situations. Therefore, a proper fixation of the catheter is of crucial importance to prevent critical situations and to allow patients to move more freely.

Adequate fixation of these catheters can be achieved using catheter fixation devices. These stabilization devices positively influence the lifetime of the catheter, decrease the number of catheter fixation procedures and the number of complications (e.g. phlebitis, extravasion or infections), all of which have been demonstrated in the scientific literature.

The fixation of epidural catheters is crucial, since only the slightest inward or outward migration of these catheters may have serious consequences on for example the efficacy of epidural analgesia. Known medical devices for securing these types of catheters are commercially available. However, these fixation means are often unwieldy and bulky. A number of known catheter fixation devices fail to adequately prevent small longitudinal movements of the catheter, also known as micro-pistoning, leading to increased risk of infections. Other known medical devices require complicated and lengthy application procedures, such as for example a large number of foils which are to be removed prior to application. The longer and the more difficult the application of these fixation devices is, the longer it takes to tightly secure the catheter after insertion into the patient. Moreover, known catheter fixation devices are often designed such as to engage with the winged portion of a catheter, but are evidently unsuitable for the fixation of wingless catheters such as epidural catheters. Finally, the fixation strength of existing fixation devices is often low.

In conclusion, there is a continuous need in the art for means for improved securement and fixation of different types of catheters, in particular wingless ones, being both compact and easy to apply while providing a sufficient amount of movement inhibition of the catheter leading to the resistance to higher pulling forces.

SUMMARY OF THE INVENTION

The present invention provides for a medical device for securing a catheter to a living creature, comprising a body member having a first side adapted to be removably attached to the living creature, a second side opposite said first side, said second side provided with a pair of posts, a channel defined in between said pair of posts and being adapted to receive said catheter and a retaining strap having an opening adapted to enclose said pair of posts in an engaged position for clamping the catheter, wherein said pair of posts is tilted towards each other in the engaged position and independently from the body member.

In an embodiment, the medical device comprises a body member having a first side adapted to be removably attached to the living creature, a second side opposite said first side, said second side provided with a pair of posts, a channel defined in between said pair of posts and being adapted to receive said catheter and a retaining strap having an opening adapted to enclose said pair of posts in an engaged position for clamping the catheter.

In some embodiments, the catheter may be an epidural catheter, a catheter for neonates or premature babies or a peripheral nerve block catheter.

In another embodiment, the second side of the body member is provided with two or more posts.

In a further embodiment, each post may independently from each other be hollow or may contain a fluid or deformable solid material. Consequently, each post may independently from each other further comprise one or more supporting ribs.

In yet another embodiment, the pair of posts may at least be partially disconnected from the body member, allowing the pair of posts to be actuated independently from at least part of the body member. In this context the word "partially disconnected" is understood as "only partially connected".

In a next embodiment, the channel may have a variable cross-sectional diameter.

In another embodiment, the channel may have a V-shaped cross-sectional diameter, the channel thereby gradually decreasing in width towards the second side of the body member.

In a following embodiment, the channel may have a U-shaped cross-sectional diameter, the channel thereby retaining the same width towards the second side of the body member.

In a further embodiment, the shape of the channel may be adapted to a specific shape of a catheter.

In yet a further embodiment, the opening may also be a recess.

In a next embodiment, the medical device for securing a catheter to a living creature is further characterized in that a tubular section of the catheter is received by said channel.

In an embodiment, the channel is suitable for receiving at least part of the tubular section of the catheter and no other parts of the catheter such as wings, . . . .

In a further embodiment, the medical device for securing a catheter to a living creature is further characterized in that at least one post of said pair of posts comprises an abutment for keeping the retaining strap in the engaged position.

In an embodiment, both posts of the pair of posts comprise an abutment.

In a following embodiment, both the pair of posts and the retaining strap comprise at least one abutment. This way, at least one of the abutments of the retaining strap may cooperate with at least one abutment of at least one post of the pair of posts for keeping the retaining strap in the engaged position. In this aspect, a single post and/or the retaining strap may comprise a plurality of abutments.

In an embodiment, the at least one abutment lies at the outer side of the at least one post, the outer side being opposite to the channel side.

In a further embodiment, the pair of posts do not comprise any abutment.

In a next embodiment, the width of each post of the pair of posts may gradually decrease towards the second side of the body member. This way, the pair of posts do not comprise any abutments for keeping the retaining strap in the engaged position.

In a further embodiment, the medical device for securing a catheter to a living creature is further characterized in that the retaining strap is connected to the body member.

In an embodiment, the retaining strap may be detachably coupled to the body member.

In another embodiment, the retaining strap may be integrally formed with the body member.

In a further embodiment, both the body member and the retaining strap can be made from a deformable solid material. This way, the medical device can be mounted to a patient while the wearing comfort can be increased. This may be particularly useful when the patient would lie down upon the attachment side of the medical device.

In yet a further embodiment, the medical device for securing a catheter to a living creature is further characterized in that the retaining strap further comprises a connecting segment which connects said retaining strap to said body member.

In an embodiment, the connecting segment may be flexible. This way, the retaining strap can be easily brought into the engaged position.

In yet a further embodiment, the medical device for securing a catheter to a living creature is further characterized in that the retaining strap further comprises a handling segment for manipulating said retaining strap from the disengaged position to the engaged position.

In an embodiment, the handling segment may comprise a recess which facilitates the grasping of said handling segment. Such facilitation may simplify the movement of the retaining strap from the disengaged position to the engaged position.

In a next embodiment, the medical device for securing a catheter to a living creature is further characterized in that the retaining strap further comprises an engaging segment comprising said opening and being positioned in between said connecting segment and said handling segment.

In an embodiment, the connecting segment, the engaging segment and the handling segment may lie in line with each other.

In a next embodiment, the medical device for securing a catheter to a living creature is further characterized in that the first side of said body member comprises an adhesive material or an adhesive sheet.

In an embodiment, the adhesive material may cover the entire surface of the first side of said body member.

In another embodiment, the adhesive sheet may at least cover the entire surface of the first side of said body member. The total surface of the adhesive sheet may for example exceed the entire surface of the first side of said body member, which increases the contact surface with the skin of the patient when applied.

In a further embodiment, the medical device for securing a catheter to a living creature is further characterized in that the pair of posts inhibits at least longitudinal movement of the catheter relative to the body member in the engaged position.

In an embodiment, the pair of posts may inhibit at least both longitudinal movement and transversal movement of the catheter relative to the body member in the engaged position.

In a next embodiment, the pair of posts may inhibit at least longitudinal movement, transversal movement and vertical movement of the catheter relative to the body member in the engaged position.

In a following embodiment, the medical device for securing a catheter to a living creature is further characterized in that the body member is adapted to conform to the shape of the application area of the living creature.

In an embodiment, the medical device may be adapted to be secured to the body of a patient. More specifically, the medical device may be for example secured to the patient's back, arm, shoulder, chest or leg.

In another embodiment, the medical device may be adapted to be secured to an animal.

In a further embodiment, the use of the medical device for securing a catheter to a living creature is disclosed.

In a next embodiment, a kit comprising the medical device for securing a catheter to a living creature, a catheter and optionally an adhesive foil is disclosed.

In a specific embodiment, the adhesive foil may cover at least part of the medical device and/or at least part of the catheter.

In an embodiment, the adhesive foil comprises an adhesive material on one side of the adhesive foil.

DETAILED DESCRIPTION OF THE INVENTION

Figure 1:
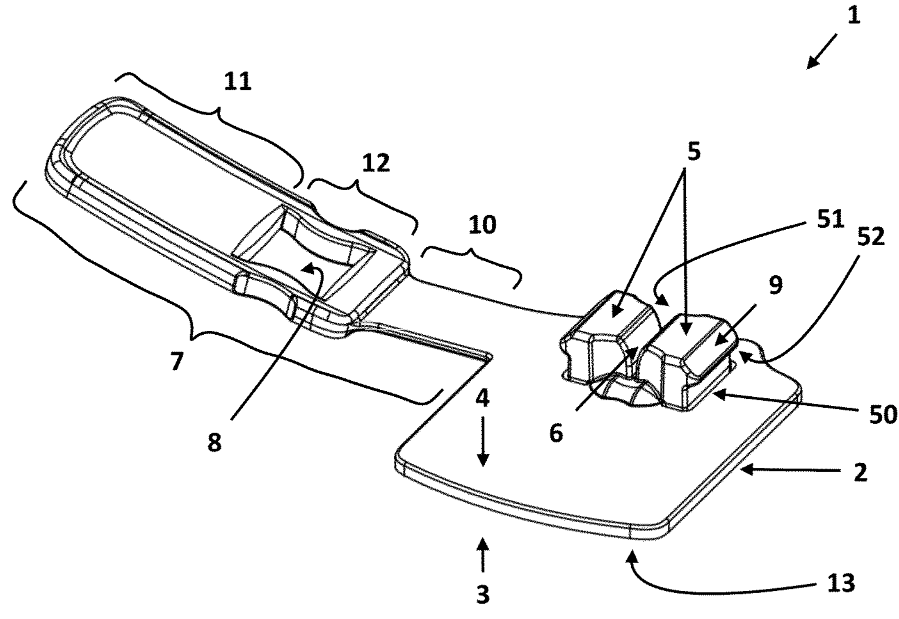
FIG. 1 is a perspective view of a medical device, according to an embodiment of the present invention.

The present invention will be described with respect to particular embodiments and with reference to certain drawings, but the invention is not limited thereto. The drawings, as further described, are only schematic and non-limiting. In the drawings, some of the elements may not be drawn to scale for illustrative purposes. The dimensions and the relative dimensions do not correspond to the actual reductions to practice of the invention.

Furthermore, the terms first, second, further and the like in the description and in the claims are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a product comprising A and B" should not be limited to devices consisting only of components A and B. It means that with respect to the present invention, the relevant components of the product are A and B, and that further components such as C may be present.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details.

In other instances, well-known methods, structures and techniques have not been shown in detail in order not to obscure an understanding of this description.

Besides that, when a part of the medical device is said to 'inhibit' movement and unless defined otherwise, the term 'inhibit' should be interpreted as partially or completely reducing movement. This term may alternatively be referred to as for example: "minimize", "constrain" or "impede".

Similarly, it is to be noticed that the term "removably attached", also used in the claims, should not be interpreted as being restricted to direct connections only. The terms "removably attached" and "connected", along with their derivatives, may be used. It should be understood that these terms are not intended as synonyms for each other. Thus, the scope of the expression "an element A removably attached to an element B" should not be interpreted as elements (e.g. medical device, skin of a patient) being preferably inseparably attached to each other, but rather as an attachment which can be breached by means of a particular pulling force. The term "connected" on the other hand, should be interpreted as describing a coupling between two elements (e.g. base element, body member) which is preferably inseparable. Thus, the scope of the expression "an element A connected to an element B" should be interpreted as an element A being preferably inseparably coupled to element B.

The following terms are provided solely to aid in the understanding of the invention. As used herein and unless otherwise specified, when a medical device is said to "secure a medical article to a support", it is meant that at least a portion of the medical article is fixed to and/or stabilized to and/or positioned onto the support. Securing the medical article typically hinders, or even completely prevents, both translational and rotational movement of at least a portion of the medical article. In the context of the present invention, the term "support" is preferably understood as being a living creature.

As used herein and unless otherwise specified, the term "living creature" is to be understood as the body of a living being, more in particular of human beings or animals. Securing the medical article to the living body advantageously reduces the risk of the medical article moving with respect to the body or even being accidentally removed therefrom.

As used herein and unless otherwise specified, the term "enclose" should be interpreted as to surround or close off an element within a two-dimensional space.

As used herein and unless otherwise specified, the term "tilted" should be interpreted as causing something to move into a sloping or uneven position or to be in this position.

As used herein and unless otherwise specified, the term "engaged position" (may hereinafter also be referred to as "closed position" or "activated position") should be interpreted as the position which enables an object to exercise its utility, with the opposite of the engaged position being the disengaged position. For example, if the retaining strap is brought into the engaged position while holding a catheter, it is meant that the medical device is clamping the catheter in order to inhibit movement thereof.

As used herein and unless otherwise specified, the term "recess" should be interpreted as a space located further back compared to the surrounding space.

It is an advantage of embodiments of the current invention that different types of catheters can be secured.

It is also an advantage of embodiments of the current invention that the medical device may be produced with techniques such as injection moulding while using only a single material.

It is a further advantage of embodiments of the current invention that different types of catheters can already be at least partially immobilised in a disengaged position.

It is an advantage of embodiments of the current invention that the medical device can be placed in close proximity to the insertion site of the catheter.

It is yet another advantage of embodiments of the current invention that the medical device may be made of a deformable material, thereby increasing wearing comfort for a patient.

It is also an advantage of embodiments of the current invention that the retaining strap can be actuated to an engaged position independently from the body member.

It is an advantage of embodiments of the current invention that the diameter of the tubular section of the catheter is not affected when actuating the retaining strap into the engaged position. This is particularly relevant to ensure a good flow of fluids running through the catheter.

It is a further advantage of embodiments of the current invention that the retaining strap can be brought repeatedly from a disengaged position to an engaged position, to allow repositioning of the catheter if needed.

It is also an advantage of embodiments of the current invention that different diameters of catheters can be fixated within the medical device. These diameters can be expressed in French or in Gauge. Epidural and peripheral nerve block catheters are generally expressed in Gauge (e.g. 18 to 20 Gauge).

It is yet a further advantage of embodiments of the current invention that higher fixation strengths can be achieved compared to existing fixation devices.

In a first aspect, the current invention provides for a medical device for securing a catheter to a living creature, comprising a body member having a first side adapted to be removably attached to the living creature, a second side opposite said first side, said second side provided with a pair of posts, a channel defined in between said pair of posts and being adapted to receive said catheter and a retaining strap having an opening adapted to enclose said pair of posts in an engaged position for clamping the catheter, wherein said pair of posts is tilted towards each other in the engaged position and independently from the body member.

In some embodiments, the medical device for securing a catheter to a living creature comprises a body member having a first side adapted to be removably attached to the living creature, a second side opposite said first side, said second side provided with a pair of posts, a channel defined in between said pair of posts and being adapted to receive said catheter and a retaining strap having an opening adapted to enclose said pair of posts in an engaged position for clamping the catheter, characterized in that the body member comprises a gap arranged at the height of the transition between the pair of posts and the second side of the body member for partially disconnecting the pair of posts and the body member to enable said pair of posts to be tilted towards each other in the engaged position independently from the body member.

In some embodiments, the first side of the base element may be removably attached to the living creature by means of an adhesive material. The adhesive material advantageously allows the first side to be easily fixed to the living creature. In preferred embodiments, the fixation may be reversible, such as by using a removable adhesive (e.g. tape, glue).

In some embodiments, the medical device comprises a pair of posts, being a total of two at least partially separate posts. Each post is positioned such as to provide for a channel in between said pair of posts, the channel being suitable for receiving a catheter.

In some embodiments, the material of the body member may be selected from the list comprising: thermoplastic elastomers, polyurethane based gels, a foam, a gel, a tacky material, a rubber more general a deformable solid material.

In some embodiments, the cross-sectional shape of the pair of posts may be selected from the list comprising: quadrangular, square, rectangular, oval or circular.

In some embodiments, the body member may be provided with a plurality of posts (e.g. 3, 4, 5 or 6). Preferably, a total amount of two posts are present.

In some embodiments, the pair of posts may be at least partially filled with a fluid, which may be selected from the list comprising: air or an oil.

In some embodiments, the pair of posts may be at least partially filled with and/or made of a deformable solid material, which may be selected from the list comprising: thermoplastic elastomers, polyurethane based gels, a foam, a gel, a tacky material, a rubber or more generally a deformable solid material.

In some embodiments, at least one post of the pair of posts may comprise at least one supporting rib. When using a technique like injection moulding, the use of supporting ribs increases the general stability and strength of the construction, in this case the at least one post. Generally, both posts of said pair of posts would comprise at least one supporting rib, which reduces the chance of collapsing of said pair of posts when applying an amount of pressure comparable to the press of a human thumb for example.

In some embodiments, the pair of posts may be partially disconnected from the body member, so that the pair of posts can be tilted towards each other in the engaged position without influencing the movement of at least part of the body member. In this context the word "partially disconnected" is understood as "only partially connected". Preferably, the connection between at least one of the posts of the pair of posts and the body member will be cut at the transition area between both parts, thereby for example resulting in an incision (hereinafter also referred to as "gap").

In other embodiments, the shape of the pair of posts and therefore the shape of the channel may be adapted in such a way to be able to receive the shape of a specific type of catheters. Preferably, the shape of the channel is adapted in such a way to be able to receive tubular-shaped catheters (e.g. epidural catheters).

Preferably, a tubular section of a catheter is received by the channel. As used herein and unless otherwise specified, the term "received" should be interpreted as the possibility of introducing one element within another element. For example, when a tubular section of a catheter is received by the channel, said channel is shaped in such a way that the tubular section of the catheter fits within the channel.

In a following aspect, the current invention provides for the medical device for securing a catheter to a living creature, further characterized in that each post of said pair of posts comprises an abutment for keeping the retaining strap in the engaged position.

In preferred embodiments, the abutments are made of the same material as the pair of posts, so that each abutment is integrally formed with the corresponding post. The abutments are generally present in order to immobilize the retaining strap. More specifically, the edges of the opening are secured underneath the abutments in such a way that at least the engaging segment of the retaining strap tightly encloses the pair of posts in the engaged position.

In a next aspect, the current invention provides for the medical device for securing a catheter to a living creature, further characterized in that the retaining strap is connected to the body member in a disengaged position.

In some embodiments, the retaining strap may be detachably coupled to the body member in a disengaged position, which enables the option of removing the retaining strap from the body member.

In preferred embodiments, both the retaining strap and the body member are made of a similar material and produced using for example injection molding. This way, the body member is integrally formed with the retaining strap, which may further positively influence the strength of the medical device as a whole.

In preferred embodiments, a deformable solid material may be used as a main material of at least the body member and the retaining strap which may be selected from the list comprising: a foam, a gel, a tacky material, a rubber or more generally a deformable solid material. The deformable solid material positively influences the wearing comfort of the patient, especially when the medical device is mounted on the patient's back and the patient would lie down in bed. The patient would, in this case, apply pressure on the medical device and the deformable solid material would allow the body member and the retaining strap to slightly deform in its entirety. As a result, the patient will experience less discomfort compared to medical devices comprising stiff, non-deformable materials.

In a further aspect, the current invention provides for the medical device for securing a catheter to a living creature, further characterized in that the retaining strap comprises a connecting segment which connects said retaining strap to said body member.

In preferred embodiments, the connecting segment may be flexible. This way, the engaging and the handling segments of the retaining strap can be brought into the engaged position by means of a pivoting motion of the connecting segment.

In yet another aspect, the current invention provides for the medical device for securing a catheter to a living creature, further characterized in that the retaining strap comprises a handling segment for manipulating said retaining strap between the disengaged position and the engaged position.

In some embodiments, the handling segment may comprise a recess. This recess simplifies the grasping of the handling segment in order to move the retaining strap into the engaged position.

In a following aspect, the current invention provides for the medical device for securing a catheter to a living creature, further characterized in that the retaining strap comprises an engaging segment comprising said opening and being positioned in between said connecting segment and said handling segment.

In preferred embodiments, the connecting segment, the engaging segment and the handling segment lie in line with each other with the connecting segment closest to the body member. This way, the opening of the engaging segment can be positioned above the pair of posts in the engaged position, which simplifies the enclosing of said pair of posts.

In a next aspect, the current invention provides for the medical device for securing a catheter to a living creature, further characterized in that the first side of said body member comprises an adhesive material or an adhesive sheet.

In some embodiments, the adhesive material may be selected from the list comprising: glue, tape or more generally an adhesive material.

In preferred embodiments, the first side of the body member may comprise an adhesive sheet which covers the entire surface of the first side of said body member. This way, the body member has a large amount of contact surface with the patient's skin in order for the body member to be tightly secured to a part of the patient's body. The adhesive sheet may be flexible such that it can conform to the shape of the patient's body. Furthermore, the adhesive sheet may also comprise an adhesive material, which may equally be selected from the list comprising: glue, tape or more generally an adhesive material.

In a further aspect, the current invention provides for the medical device for securing a catheter to a living creature, further characterized in that the pair of posts inhibits at least longitudinal movement of the catheter relative to the body member in the engaged position.

The inhibition of at least longitudinal movement entails that at least the tubular section of the catheter, which is fixed within the channel of the medical device, cannot be displaced when the medical device is moved in the engaged position, even when a pulling force is exerted upon the catheter.

In a further aspect, the current invention provides for the medical device for securing a catheter to a living creature, further characterized in that the body member is adapted to conform to the living creature. If the medical device would be mounted to a patient's arm, the body member can conform to the shape of the arm, so that the entire first side of the body member can contact the patient's skin.

We now refer to FIG. 1, showing a perspective view of a medical device 1 in accordance with an embodiment of the present invention. In the current figure, the medical device 1 is disclosed in a disengaged position, meaning that a catheter 60 (not shown) can be accepted by the medical device 1. The medical device 1 comprises a body member 2 having a first side 3 for securing the medical device 1 to a living creature (e.g. an arm or the back of a patient) and a second side 4 opposite the first side 3. The body member 2 is slightly flexible such that it can conform to the shape of the living creature and can be removably coupled to the living creature using an adhesive material 13 (e.g. glue or tape). The adhesive material 13 is connected to the first side 3 of the body member 2. The body member 2 is further made of a deformable solid material (e.g. thermoplastic elastomers or polyurethane based gel) which allows the body member 2 to at least partially conform to the living creature, providing a sufficient amount of flexibility to the body member 2, such that the body member 2 is able to slightly deform in its entirety, for example when the patient is applying pressure on the medical device 1 by lying on the medical device 1. Because of this feature, the patient will experience noticeably less discomfort compared to medical devices consisting of stiff, non-deformable materials. Moreover, the second side 4 of the body member 2 comprises a pair of posts 5 having abutments 9, the pair of posts 5 being partially connected to the body member 2. These pair of posts 5 define a channel 6 in between the pair of posts 5, being of sufficient size so as to receive the catheter 60. When in the disengaged position, the channel 6 is able to accept the catheter 60 and to already at least partially immobilize said catheter 60. Because of that, the catheter 60 can be already at least partially fixed immediately after the application to the patient. Furthermore, a retaining strap 7 is connected to the body member 2. The retaining strap 7 comprises a connecting segment 10, a handling segment 11 and an engaging segment 12. The engaging segment 12 further comprises an opening 8 which is adapted to tightly enclose said pair of posts 5 in the engaged position for clamping the catheter 60. In this example, the channel 6 is generally V-shaped, meaning that the width of the channel 6 decreases towards the second side 4 of the body member 2 in the disengaged position. This way, when the catheter 60 is received by the channel 6 and when the retaining strap 7 is moved into the engaged position, the catheter 60 may be guided slightly towards the second side 4 of the body member 2. This can be accomplished because of the fact that the pair of posts 5 are tilted towards each other in the engaged position, effectuated by the clamping force generated by the opening 8 of the retaining strap 7. When the pair of posts 5 are tilted towards each other, the channel sides 51 of the pair of posts 5 apply a certain pressure or clamping force upon the catheter 60. The tilting motion of the pair of posts 5 happens independently from the body member 2 since said pair of posts 5 and the body member 2 are partially disconnected. This partially disconnecting is arranged by the gap 50. This gap 50 is present at the height of the transition between the pair of posts 5 and the second side 4 of the body member 2. In this context the word "at the height of" is understood as "at the location of" or "a proximity of". So, when the medical device 1 is secured to for example the arm of a patient, the pair of posts 5 can be tilted inwardly and independently from the body member 2. This enables the tight securement of the catheter 60 within the channel of the medical device 1 even when the medical device 1 is secured to a curved surface (e.g. arm of a patient). In this engaged position, the pair of posts 5 at least partially enclose the catheter 60 and exert a force upon the catheter 60. This way, at least the longitudinal movement of the catheter 60 is inhibited in the engaged position by the medical device 1. In this engaged position, it is not possible to remove the catheter 60 from the channel 6, because of the cooperation of the retaining strap 7, the channel 6 and the pair of posts 5, together inhibiting the vertical movement of the catheter 60.

Figure 2:
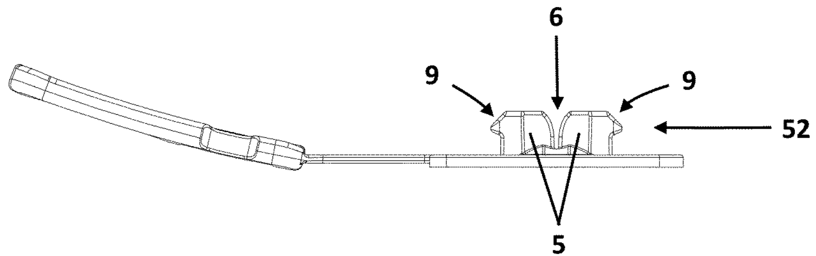
FIG. 2 is a front view of a medical device, according to an embodiment of the present invention.

We now refer to FIG. 2, showing a front view of a medical device 1 in accordance with an embodiment of the present invention. This figure clearly shows the V-shape of the channel 6 of the medical device 1. Furthermore, the pair of posts 5 comprise abutments 9 which are in this example part of the pair of posts 5. The abutments 9 are present at the outer side 52 of the pair of posts 5 and will allow the opening 8 of the retaining strap 7 to be secured underneath these abutments 9. The retaining strap 7 is slightly deformable. Hence, when the retaining strap 7 is gripped and pulled at to be moved to the engaged position, the opening 8 of the retaining strap 7 slightly enlarges and encloses the pair of posts 5. When the retaining strap 7 is released, the opening 8 slightly decreases in size and causes the pair of posts 5 to be tilted towards each other to tightly secure the catheter 60 (not shown). The abutments 9 prevent the engaging segment 12 of the retaining strap 7 to return to the disengaged position. This way, the retaining strap 7 is tightly held into place by the abutments 9.

Figure 3:
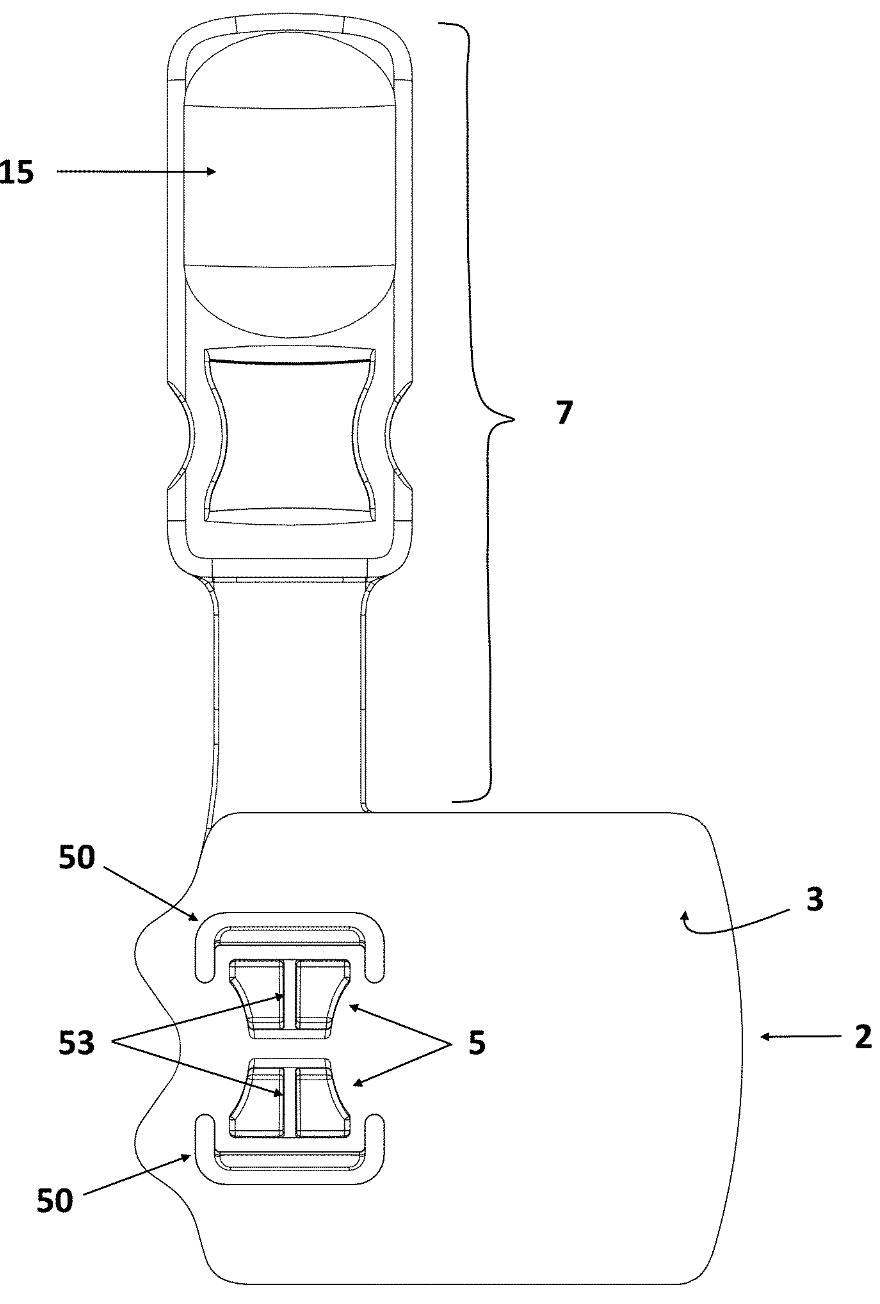
FIG. 3 is a bottom view of a medical device, according to an embodiment of the present invention.

We now refer to FIG. 3, showing a bottom view of a medical device 1 in accordance with an embodiment of the present invention. This figure clearly shows the first side 3 of the body member 2, comprising two gaps 50, one besides each post of the pair of posts 5, which makes that the pair of posts 5 are only partially connected to the body member 2. Besides that, each post of the pair of posts 5 comprises a supporting rib 53 in order to further increase the strength of said pair of posts 5. Further, the handling segment of the retaining strap 7 is shown to comprise a recess 15 which facilitates the grasping of said handling segment.

Figure 4A:
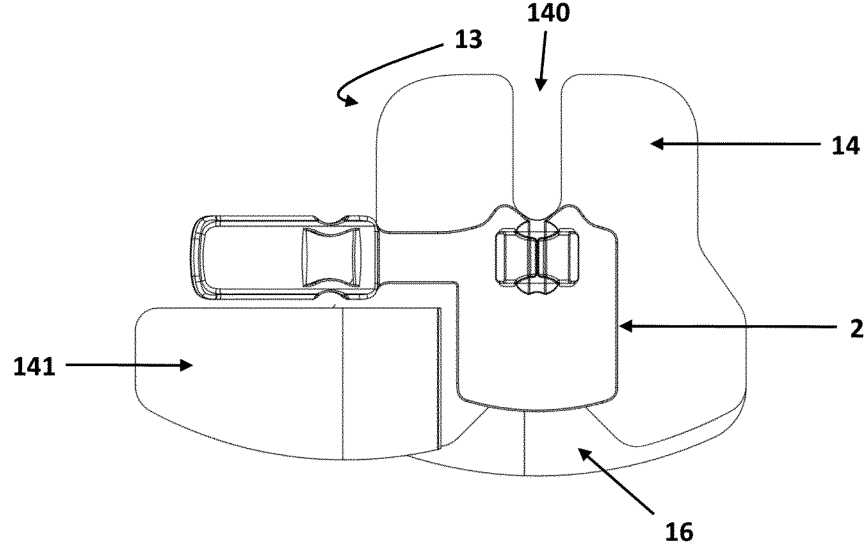
FIG. 4A is a top view of a medical device, including an adhesive sheet, wherein the strap is in a disengaged position, according to an embodiment of the present invention.
Figure 4B:
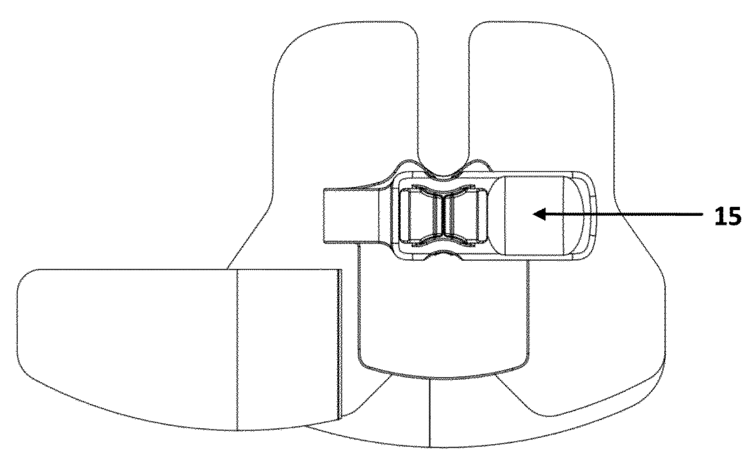
FIG. 4B is a top view of a medical device including an adhesive sheet, wherein the strap is in an engaged position, according to an embodiment of the present invention.

We now refer to FIGS. 4A and 4B, showing top views of a medical device 1 including an adhesive sheet 14, the retaining strap 7 being respectively in a disengaged position and in an engaged position in accordance with an embodiment of the present invention. The medical device 1 comprises an adhesive sheet 14 having an adhesive material 13 present on the side of the adhesive sheet 14 opposite the body member 2. The surface of the adhesive sheet 14 exceeds the surface of the body member 2 and is generally winged-shaped. A notch 140 is present which enables the medical device 1 to be placed in close proximity to the catheter 60 insertion site of the patient. This way, the adhesive sheet 14 does not contact nor interfere with the catheter 60. Furthermore, the adhesive material 13 is covered with an adhesive cover 16, which is to be removed prior to the application of the medical device 1 to the patient. When the adhesive cover 16 is removed, the adhesive material 13 (e.g., glue or tape) becomes exposed. Further, the handling segment of the retaining strap 7 is shown to comprise a recess 15 which facilitates the grasping of said handling segment. Such facilitation may simplify the movement of the retaining strap from the disengaged position to the engaged position.

The adhesive sheet 14 further comprises an adhesive strap 141 which can be placed over the catheter 60 when the medical device is in the engaged position in order to further cover and secure the catheter 60. As seen on FIG. 4B, which visualizes the engaged position of the medical device 1, the adhesive strap 141 is not yet moved over the body member 2.

Figure 5:
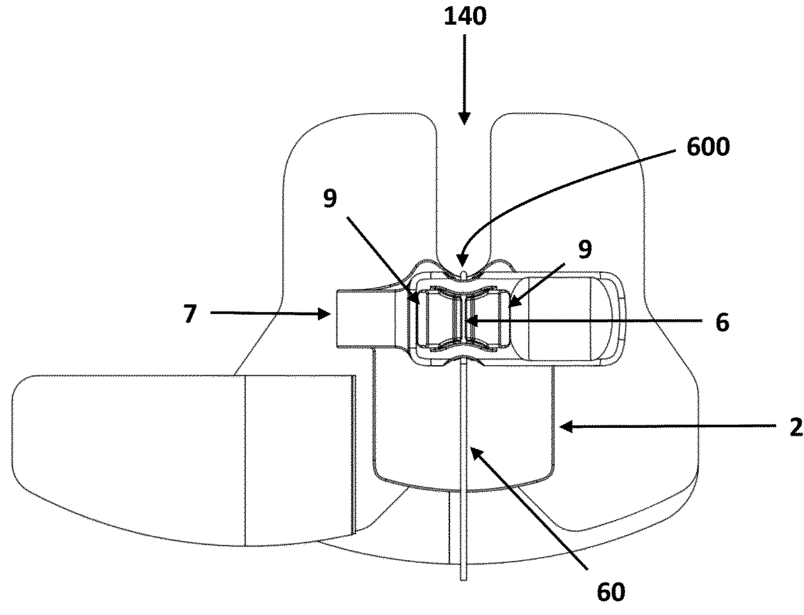
FIG. 5 is a top view of a medical device, including an adhesive sheet, showing the securing of a catheter, according to an embodiment of the present invention.

We now refer to FIG. 5, showing a top view of a medical device 1 including an adhesive sheet 14 securing a catheter 60 in accordance with the present invention. The catheter insertion site 600 is visible and the notch 140 of the adhesive sheet 14 allows the medical device 1 and more specifically the body member 2 of the medical device 1 to be place in close proximity to said catheter insertion site 600. The catheter 60 is secured by the body member 2 within the channel 6 in between the pair of posts 5. The opening 8 of the retaining strap 7 encloses the pair of posts 5 and the pair of posts 5 are tilted towards each other. The abutments 9 are secured over the edges of the opening 8, holding the retaining strap 7 in the engaged position.

Figure 6:
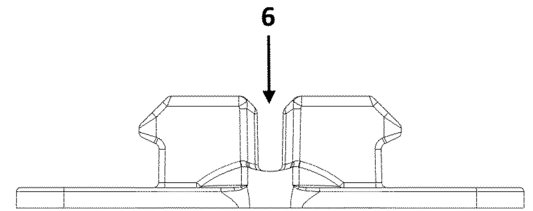
FIG. 6 is a front view of a medical device, according to an embodiment of the present invention.

We now refer to FIG. 6, showing a front view of a medical device 1 in accordance with an embodiment of the present invention. In this example, the channel 6 of the body member 2 is U-shaped, meaning that the width of the channel 6 does not decrease towards the second side 4 of the body member 2 in the disengaged position but is the same along the entire height of the channel 6.

LIST OF FEATURES

| Number | Feature |
|---|---|
| 1 | Medical device |
| 2 | Body member |
| 3 | First side (of the body member) |
| 4 | Second side (of the body member) |
| 5 | Pair of posts |
| 6 | Channel |
| 7 | Retaining strap |
| 8 | Opening |
| 9 | abutments |
| 10 | Connecting segment |
| 11 | Handling segment |
| 12 | Engaging segment |
| 13 | Adhesive material |
| 14 | Adhesive sheet |
| 15 | recess |
| 16 | Adhesive cover |
| 50 | gap |
| 51 | Channel side |
| 52 | Outer side |
| 53 | Supporting rib |
| 60 | catheter |
| 140 | notch |
| 141 | Adhesive strap |
| 600 | Catheter insertion site |

The invention claimed is:

1. A medical device for securing a catheter to a living creature, the medical device comprising:

a body member having a first side and a second side, the first side adapted to be removably attached to the living creature;

a pair of posts extending from the second side and having a channel therebetween adapted to receive the catheter; and a retaining strap having an opening adapted to enclose the pair of posts when in an engaged position for clamping the catheter, wherein the body member further comprises a first gap extending from the first side to the second side and arranged near a base of a first post of the pair of posts so as to permit the first post to be tilted toward a second post of the pair of posts in the engaged position, independently of those portions of the body member that are attached to the living creature.

2. The medical device according to claim 1, wherein the channel is adapted to receive a tubular section of the catheter.

3. The medical device according to claim 1, wherein at least one post of the pair of posts comprises an abutment for keeping the retaining strap in the engaged position.

4. The medical device according to claim 1, wherein the retaining strap is connected to the body member in a disengaged position of the retaining strap.

5. The medical device according to claim 1, wherein the retaining strap further comprises a connecting segment that connects the retaining strap to the body member.

6. The medical device according to claim 1, wherein the retaining strap further comprises a handling segment for manipulating the retaining strap from a disengaged position to the engaged position.

7. The medical device according to claim 1, wherein the first side of the body member comprises an adhesive material or an adhesive sheet.

8. The medical device according to claim 1, wherein the pair of posts inhibits at least longitudinal movement of the catheter relative to the body member in the engaged position of the retaining strap.

9. The medical device according to claim 1, wherein the body member is adapted to conform to the living creature.

10. The medical device according to claim 1, wherein the retaining strap further comprises a connecting segment that connects the retaining strap to the body member; and wherein the retaining strap further comprises a handling segment for manipulating the retaining strap from a disengaged position to the engaged position.

11. The medical device according to claim 10, wherein the retaining strap further comprises an engaging segment comprising the opening and being positioned between the connecting segment and the handling segment.

12. The medical device according to claim 1, further comprising a second gap extending from the first side to the second side and arranged near a base of the second post of the pair of posts so as to permit the second post to be tilted toward the first post in the engaged position independently of those portions of the body member that are attached to the living creature.

13. A method for securing a catheter to a living creature with the medical device according to claim 1, the method comprising:

attaching the first side of the body member of the medical device to the living creature;

placing the catheter in the channel of the medical device; and moving the retaining strap of the medical device into the engaged position.

14. A kit comprising:

the medical device according to claim 1; and a catheter.

15. The kit according to claim 14, further comprising an adhesive foil.

* * * * *